(12) United States Patent
Kadomura et al.

(10) Patent No.: US 9,129,389 B2
(45) Date of Patent: Sep. 8, 2015

(54) X-RAY CT APPARATUS AND IMAGE CORRECTION METHOD

(71) Applicants: Takayuki Kadomura, Tokyo (JP); Hiroto Kokubun, Tokyo (JP)

(72) Inventors: Takayuki Kadomura, Tokyo (JP); Hiroto Kokubun, Tokyo (JP)

(73) Assignee: HITACHI MEDICAL CORPORATION, Tokyo (JP)

( * ) Notice: Subject to any disclaimer, the term of this patent is extended or adjusted under 35 U.S.C. 154(b) by 0 days.

(21) Appl. No.: 14/239,867

(22) PCT Filed: Sep. 24, 2012

(86) PCT No.: PCT/JP2012/074397
§ 371 (c)(1),
(2) Date: Feb. 20, 2014

(87) PCT Pub. No.: WO2013/047439
PCT Pub. Date: Apr. 4, 2013

(65) Prior Publication Data
US 2014/0212016 A1 Jul. 31, 2014

(30) Foreign Application Priority Data
Sep. 27, 2011 (JP) .................................. 2011-210120

(51) Int. Cl.
*G06K 9/00* (2006.01)
*G06T 5/00* (2006.01)
*A61B 6/03* (2006.01)
*G06T 11/00* (2006.01)
*A61B 6/00* (2006.01)

(52) U.S. Cl.
CPC ................. *G06T 5/009* (2013.01); *A61B 6/032* (2013.01); *A61B 6/481* (2013.01); *A61B 6/486* (2013.01); *A61B 6/503* (2013.01); *A61B 6/5258* (2013.01); *A61B 6/541* (2013.01); *A61B 6/545* (2013.01); *G06T 11/005* (2013.01); *A61B 6/461* (2013.01); *A61B 6/466* (2013.01); *A61B 6/5288* (2013.01)
(Continued)

(58) Field of Classification Search
CPC ................................ A61B 6/032; A61B 6/481
USPC ............. 382/131, 132; 378/23, 125; 600/413, 600/425–429
See application file for complete search history.

(56) References Cited

U.S. PATENT DOCUMENTS 6,674,444 B1 * 1/2004 Tahara .......................... 345/589
7,352,840 B1 * 4/2008 Nagarkar et al. ............... 378/19
(Continued)

FOREIGN PATENT DOCUMENTS

| JP | 2004-57506 | 2/2004 |
|---|---|---|
| JP | 2006-21022 | 1/2006 |
| JP | 2006-326078 | 12/2006 |

OTHER PUBLICATIONS

International Search Report in PCT/JP2012/074397.

*Primary Examiner* — Samir Ahmed
(74) *Attorney, Agent, or Firm* — Cooper & Dunham LLP

(57) ABSTRACT

There is provided an X-ray CT apparatus capable of correcting the unevenness of the contrast concentration due to discontinuities in time between slices in contrast imaging using a Prospective Triggering method. In an X-ray CT apparatus 1, projection data in a specific phase of the heart is obtained by performing a scan by emitting X-rays after a predetermined time from the detection of the R wave of electrocardiogram information at each position of the heart in the body axis direction. An image processing device 4 reconstructs a tomographic image on the basis of collected projection data, calculates the projection data collection time in each scan from electrocardiogram information collected from an electrocardiograph 5, calculates the time between scans on the basis of the calculated projection data collection time, and corrects a concentration difference so as to change smoothly for an image of a position in the body axis direction in a range according to the time between scans.

14 Claims, 15 Drawing Sheets

(56) References Cited

U.S. PATENT DOCUMENTS

| | | | |
|---|---|---|---|
| 7,840,255 B2* | 11/2010 | Ichihara | 600/425 |
| 8,768,031 B2* | 7/2014 | Mistretta et al. | 382/131 |
| 2003/0097076 A1* | 5/2003 | Nambu et al. | 600/504 |
| 2004/0114717 A1 | 6/2004 | Kato | |
| 2005/0065430 A1* | 3/2005 | Wiethoff et al. | 600/413 |
| 2005/0277830 A1 | 12/2005 | Ichihara | |
| 2008/0310582 A1* | 12/2008 | Flohr et al. | 378/5 |
| 2009/0022271 A1* | 1/2009 | Ohishi et al. | 378/19 |
| 2009/0141854 A1* | 6/2009 | Hirokawa et al. | 378/4 |
| 2011/0213242 A1* | 9/2011 | Budoff et al. | 600/425 |
| 2011/0257519 A1* | 10/2011 | Bj?rnerud et al. | 600/431 |

* cited by examiner

X-RAY CT APPARATUS AND IMAGE CORRECTION METHOD

TECHNICAL FIELD

The present invention relates to an X-ray CT apparatus, and in particular, to an X-ray CT apparatus and the like to perform scanning and reconstruction using electrocardiogram information of an object collected from an electrocardiograph.

BACKGROUND ART

The X-ray CT apparatus emits X-rays while rotating an X-ray source and an X-ray detector, which is disposed so as to face the X-ray source, around an object, detects X-rays transmitted through the object over the entire circumference, and performs image reconstruction on the basis of the obtained projection data to obtain a tomographic image. In this image reconstruction, it is a requirement that the object or the organ in the object be stationary. If the object or the organ moves while collecting projection data, the target is not correctly imaged at the time of image reconstruction. As a result, a blurred image (motion artifacts) is obtained.

In particular, since the heart is an organ that is constantly beating, time to collect projection data, that is, time resolution needs to be improved in order to obtain an image of a stationary heart. Therefore, in cardiac imaging using an X-ray CT apparatus, an ECG-gated reconstruction method is performed in which an electrocardiograph is mounted on an object, projection data of the phase at which the motion of the heart is small is collected using the electrocardiogram information of the object, and image reconstruction is performed to obtain an image of the relatively stationary heart.

An imaging method in cardiac imaging using an X-ray CT apparatus is largely divided into two methods of the Retrospective Gating method and the Prospective Triggering method.

The Retrospective Gating method is a method in which a helical scan is performed while collecting electrocardiogram information of the object, only projection data of the phase at which the motion is small is collected from the obtained projection data using the electrocardiogram information, and image reconstruction is performed as described previously. In this method, since X-rays are continuously emitted to perform a helical scan, it is possible to generate an image of an arbitrary phase. However, since it is necessary to collect projection data of the same phase from a plurality of cardiac beats, the moving speed of the table is reduced. Accordingly, the amount of exposure is several times the normal helical scan.

The Prospective Triggering method is a method in which the electrocardiogram information of an object is monitored and X-rays are emitted only after a time, at which a specific phase set in advance is obtained, from the detection of an R wave, for example, to perform an axial scan. In this case, since X-rays are emitted only in a specific phase without emitting X-rays continuously, the amount of exposure is very small compared with the Retrospective Gating method (PTL 1).

Although each method has advantages and disadvantages, it is desirable to perform imaging using the Prospective Triggering method with less exposure when a burden on the object is taken into consideration.

CITATION LIST

Patent Literature

[PTL 1] JP-A-9-24045

SUMMARY OF INVENTION

Technical Problem

In the Prospective Triggering method described above, however, a scan is performed only once at the same position in the body axis direction. Therefore, in a scan of the next position in the body axis direction, projection data is collected from cardiac beats that are different from the previous scan. For this reason, there is a portion, which is not continuous in time, between slices.

Accordingly, when coronary angiography imaging is performed using the Prospective Triggering method, the concentration of the contrast medium changes greatly at a portion that is not continuous in time. As a result, when generating a Multi Planar Reconstruction (MPR) image, an uncomfortable image is obtained. In addition, even if extraction of the coronary artery is tried by image processing, the coronary artery may not be correctly extracted due to rapid changes in the concentration of the contrast.

The invention has been made in view of the above problem, and it is an object of the invention to provide an X-ray CT apparatus and the like capable of correcting the unevenness of the contrast concentration due to discontinuities in time between slices in contrast imaging using the Prospective Triggering method.

Solution to Problem

In order to achieve the object described above, a first invention is an X-ray CT apparatus that acquires a tomographic image of an object by collecting electrocardiogram information of the object from an electrocardiograph, performing a scan in synchronization with the collected electrocardiogram information, and reconstructing projection data obtained by the scan. The X-ray CT apparatus includes: a data collection unit that acquires projection data in a specific phase of a heart intermittently in a plurality of time phases in each position of the heart in a body axis direction by emitting X-rays at a predetermined timing to perform a scan; a reconstruction unit that reconstructs a tomographic image at each position in the body axis direction on the basis of the projection data acquired by the data collection unit; correction unit that calculates a time between scans from a certain scan to a next scan and corrects a concentration difference, which occurs between respective tomographic images, for a tomographic image of a body-axis-direction range determined according to a length of the calculated time between scans; and a display unit that displays an image generated on the basis of the tomographic image corrected by the correction unit.

In addition, a second invention is an image correction method in an X-ray CT apparatus that acquires a tomographic image of an object by collecting electrocardiogram information of the object from an electrocardiograph, performing a scan in synchronization with the collected electrocardiogram information, and reconstructing projection data obtained by the scan. The image correction method includes: a data collection step of acquiring projection data in a specific phase of a heart intermittently in a plurality of time phases in each position of the heart in a body axis direction by emitting X-rays at a predetermined timing to perform a scan; a reconstruction step of reconstructing a tomographic image at each position in the body axis direction on the basis of the acquired projection data; a correction step of calculating a time between scans from a certain scan to a next scan and correcting a concentration difference, which occurs between respective tomographic images, for a tomographic image of a bodyaxis-direction range determined according to a length of the calculated time between scans; and a display step of displaying an image generated on the basis of the corrected tomographic image.

Advantageous Effects of Invention

By the X-ray CT apparatus and the image correction method of the invention, it is possible to correct concentration unevenness due to discontinuities in time between slices in contrast imaging using the Prospective Triggering method. As a result, it is possible to easily perform image processing, such as processing for extracting an MPR image or a target part without discomfort.

DESCRIPTION OF EMBODIMENTS

Hereinafter, preferred embodiments of the invention will be described in detail with reference to the accompanying drawings.

Embodiments

Figure 1:
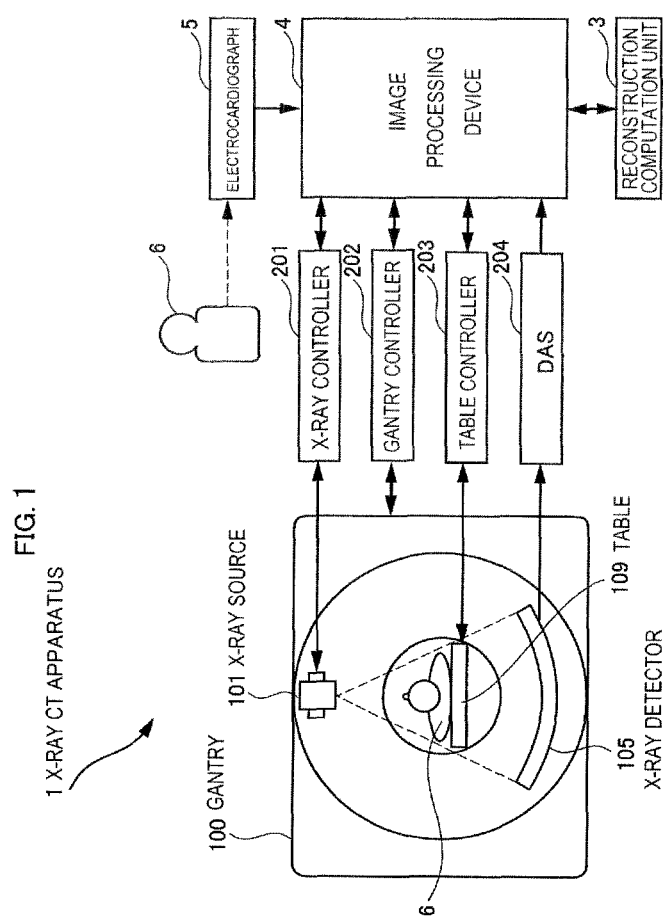
FIG. 1 is a block diagram of an X-ray CT apparatus 1.

First, the configuration of an X-ray CT apparatus 1 will be described with reference to FIG. 1.

The X-ray CT apparatus 1 includes: a gantry 100; an X-ray controller 201 that controls the irradiation of X-rays; a gantry controller 202 that controls the operation of the gantry 100; a table controller 203 that controls the operation of a table 109; a data acquisition system (DAS) 204 that collects data by converting the intensity of X-rays incident on an X-ray detector 105 into an electrical signal; a reconstruction computation unit 3 that acquires the electrical signal converted by the DAS 204 and performs correction and image reconstruction of the acquired data; an electrocardiograph 5 that collects the electrocardiogram information of the object 6; and an image processing device 4 that acquires the electrocardiogram information measured by the electrocardiograph 5 and that controls the X-ray controller 201, the gantry controller 202, the table controller 203, and the DAS 204 to perform a scan by the gantry 100 and to acquire a tomographic image reconstructed by the reconstruction computation unit 3.

In the gantry 100, an X-ray source 101 and an X-ray detector 105 are disposed so as to face each other with the table 109 on which the object 6 is placed interposed therebetween.

The X-ray source 101 is controlled by the X-ray controller 201, and emits X-rays having a predetermined intensity. The X-ray detector 105 detects X-rays, which are emitted from the X-ray source 101 and are transmitted through the object 6, and generates an electrical signal according to the intensity of the detected transmitted X-rays. During the scan, the X-ray source 101 and the X-ray detector 105 rotate around the center of rotation according to a control signal input from the gantry controller 202.

The operations of the X-ray source 101 and the gantry 100 are controlled by the X-ray controller 201 and the gantry controller 202, respectively. The X-ray controller 201 supplies a power signal and an X-ray generation timing signal to the X-ray source 101. The gantry controller 202 controls the rotation speed and position of the gantry 100. The table 109 is controlled by the table controller 203. The table controller 203 controls the moving speed and position of the table 109.

The transmitted X-rays incident on the X-ray detector 105 are converted into a digital signal by the PAS 204, and are transmitted to the image processing device 4 as digital data.

When the digital data is acquired from the image processing device 4, the reconstruction computation unit 3 generates projection data by performing data correction processing, such as sensitivity correction, logarithmic transformation, and offset correction, and performs image reconstruction processing using the projection data. The image data (tomographic image) reconstructed by the image reconstruction processing is input to the image processing device 4, and is stored in a data recording device 403 (FIG. 2) and is displayed on an image display device 405.

Figure 2:
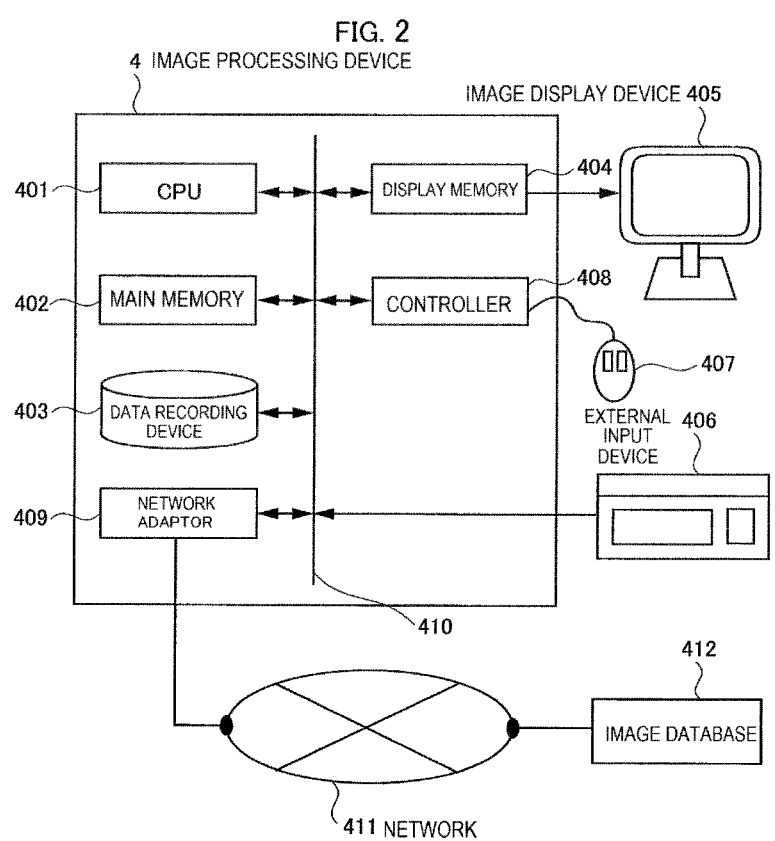
FIG. 2 is a block diagram of an image processing device 4.

FIG. 2 is a block diagram of the image processing device 4.

The image processing device 4 is configured to mainly include: a central processing unit (CPU 401) that controls the operation of each component described above; a main memory 402 in which a control program of the image processing device 4 is stored; the data recording device 403 that stores image data; a display memory 404 that stores the image data of the object 6 temporarily; the image display device 405 that performs display based on the image data stored temporarily in the display memory 404; a pointing device 407 and a controller 408, such as a mouse and a touch panel for operating soft switches on the image display device 405; an external input device 406, such as a keyboard including keys or switches for setting of various parameters; a network adaptor 409 for connecting the image processing device 4 to networks, such as a local area network, a telephone line, and the Internet; and a data bus 410 that connects the above-described components to each other. The data recording device 403 may be a storage device, such as a magnetic disk, or a device that writes or reads data into or from removable external media. The image processing device 4 may be connected to an external image database 412 through the network adaptor 409 and a network 411, so that image data is transmitted and received to and from the image database 412.

The electrocardiograph 5 measures electrocardiogram information, which indicates a time variation of the action potential reflecting the cardiac motion of the heart, through electrodes attached to the object 6, and converts the electrocardiogram information into a digital signal at predetermined sampling pitches, such as 0.1 second intervals, for example. The electrocardiogram information acquired by the electrocardiograph 5 is sequentially transmitted to the image processing device 4.

Next, the operation of the X-ray CT apparatus 1 will be described with reference to FIG. 3.

Figure 3:
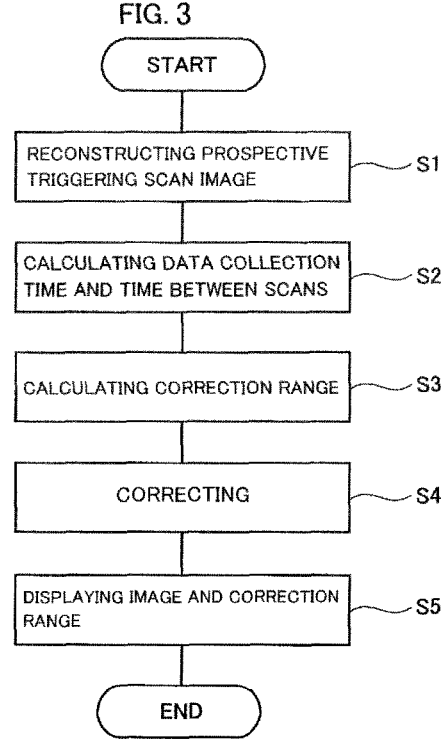
FIG. 3 is a flowchart showing the operation procedure of the X-ray CT apparatus 1.

The X-ray CT apparatus 1 of the present embodiment performs ECG-gated imaging according to the procedure shown in the flowchart of FIG. 3. That is, the CPU 401 of the image processing device 4 reads a program and data regarding the ECG-gated imaging processing shown in FIG. 3 from the main memory 402, and performs processing on the basis of the program and data.

In this processing, contrast imaging of the coronary artery is performed using the Prospective Triggering Scan method. The image processing device 4 collects projection data of the stationary phase of the heart, and performs image reconstruction using the collected projection data (step S1).

Figure 4:
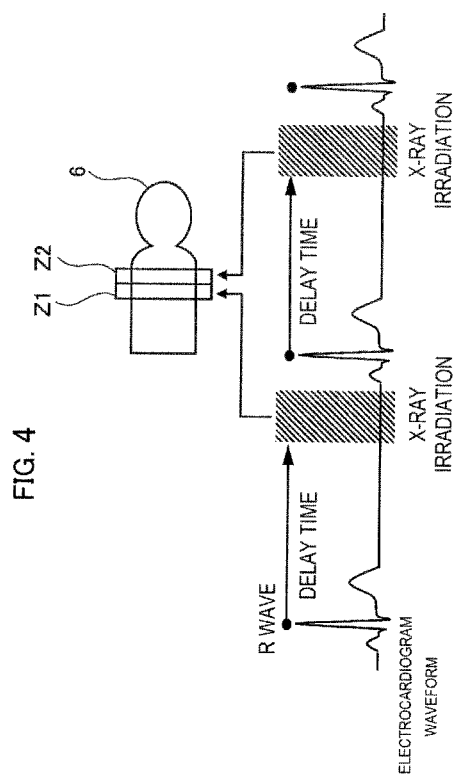
FIG. 4 is a conceptual diagram illustrating the relationship among the electrocardiogram waveform, delay time, and X-ray irradiation timing in Prospective Triggering Scan.

In the Prospective Triggering Scan, the X-ray CT apparatus 1 receives the setting regarding which phase is to be scanned for the cardiac information of the object 6, as the setting of the delay time from the arbitrary reference phase, for example, the R wave, in advance before scanning. During the scan, the image processing device 4 monitors the electrocardiogram information of the object 6, and performs controls to emit X-rays after the delay time from the detection of the R wave as shown in FIG. 4.

After the above-described delay time from the detection of the R wave, the X-ray CT apparatus 1 performs a scan by emitting X-rays to a position Z1 in the body axis direction. Then, the table 109 is moved to the next position Z2 in the body axis direction, and X-rays are emitted again after the delay time from the detection of the R wave to perform a scan.

Figure 5:
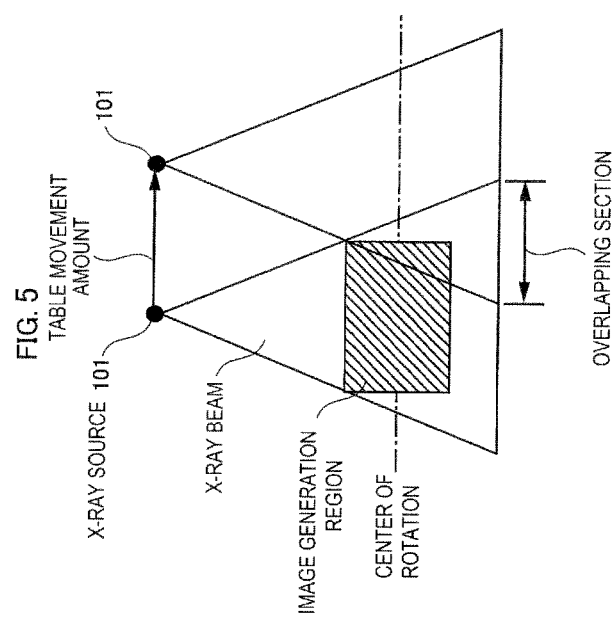
FIG. 5 is a conceptual diagram illustrating the relationship between the shape of X-rays and the table movement amount.

In this case, in the X-ray CT apparatus 1 having the X-ray detector 105 of multiple columns of, for example, 64 slices or more, the shape of X-rays is a conical shape. However, in order to maintain the continuity of the reconstructed image in the body axis direction, it is preferable to set an overlapping section in an X-ray irradiation region between scans by making the table movement amount between scans of different data collection time shorter than the X-ray irradiation width at the center of rotation of the gantry 100 as shown in FIG. 5. In addition, it is also preferable to set the number of slices (image generation regions) to reconstruct an image so as to be less than the number of slices of the X-ray detector 105.

The reconstruction computation unit 3 performs image reconstruction on the basis of the projection data obtained as described above. Through the above processing, a tomographic image in a specific phase (after R wave detection, after predetermined delay time) of electrocardiogram information is intermittently obtained over a plurality of time phases (data collection time).

Figure 6:
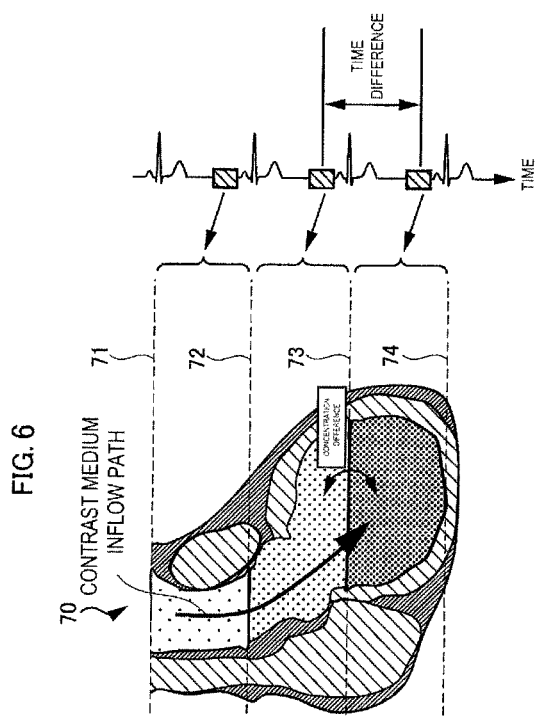
FIG. 6 is a conceptual diagram illustrating the boundary position between scans and concentration unevenness.

When an MPR image is generated using the tomographic image obtained as described above, an unnatural concentration difference occurs in the body axis direction as in an image 70 shown in FIG. 6. This is because one MPR image 70 is generated using the projection data at different cardiac beats, that is, different data collection time. Since there is a time difference between cardiac beats, a change in the concentration of the contrast medium also occurs. As a result, concentration difference becomes large in boundary slices 71, 72, 73, and 74 between scans of the different time phases (data collection time), and this becomes concentration unevenness.

In order to prevent the occurrence of such concentration unevenness, in the invention, correction processing is performed in the procedure of steps S2 to S4.

First, the image processing device 4 calculates the data collection time of each scan and a time between scans (step S2).

The data collection time is the collection time of projection data in each scan. In addition, the image processing device 4 calculates a time (time between scans) between a certain scan (k-th scan) and the next scan ((k+1)-th scan).

In the Prospective Triggering Scan, a scan (data collection) is performed at each position in the body axis direction with the passage of a predetermined delay time from the detection of the R wave as a trigger. Accordingly, a slice that is discontinuous in time occurs in the body axis direction.

In order to calculate the time between scans, first, the CPU of the image processing device 4 calculates a time from the data collection time (scan start time) of the first scan to the data collection time of each scan.

Figure 7:
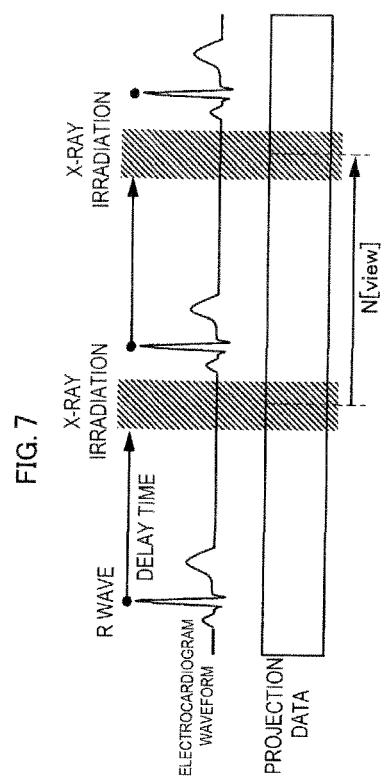
FIG. 7 is a conceptual diagram illustrating a method of calculating the time between scans.

As shown in FIG. 7, projection data is collected by making each view of projection data and electrocardiogram information correspond to each other in time, and the number of views from the center of the view range (shaded portion in FIG. 7), in which X-rays are emitted first, to the center of the view range where X-rays are emitted in each scan is calculated, for example. Then, by converting the calculated number of views into the time, the time required from the first scan to each scan is calculated. The time required from the first scan to each scan (IT [ms]) can be calculated from the rotation time per rotation of the scanner (ST [ms/rot]), the number of views acquired per rotation of the scanner in the rotation time (view rate: VP [view/rot]), and the number of views between scans obtained previously (N [view]) using the following Expression (1).

[Expression 1]

$$IT = N \times \frac{ST}{VR} \qquad (1)$$

In addition, in the example shown in FIG. 7, the reference position for calculating the time from the first scan to each scan is set to a center to center of the view range where X-rays are emitted. However, the reference position may be the start position or the end position of the view range without being limited thereto.

The time between scans is calculated by subtracting the time IT of each scan from the first scan calculated as described above from the time IT of another scan. In addition, the time between scans may be expressed as the number of R waves instead of the time.

Then, the image processing device 4 calculates a body-axis-direction range (hereinafter, referred to as a correction range) of the tomographic image to perform image correction (step S3).

The image processing device 4 determines an appropriate correction range according to the time between scans calculated in step S2.

Hereinafter, an example of the method of calculating a correction range will be described with reference to FIGS. 8 and 9.

When the time between scans calculated in step S2 is short, it is expected that the change in the concentration of the contrast medium is relatively small, as shown in FIG. 8(A). In this case, by narrowing the correction range with a boundary position between scans 80 as the center as shown in FIG. 8(B), image correction is performed so that the amount of contrast medium is viewed so as to change smoothly along the body axis direction.

On the other hand, when the time between scans calculated in step S2 is long, it is expected that the change in the concentration of the contrast medium large, as shown in FIG. 9(A). In this case, by widening the correction range with the boundary position between scans 90 as the center as shown in FIG. 9(B), image correction is performed so that the amount of contrast medium viewed so as to change smoothly along the body axis direction.

Figure 8:
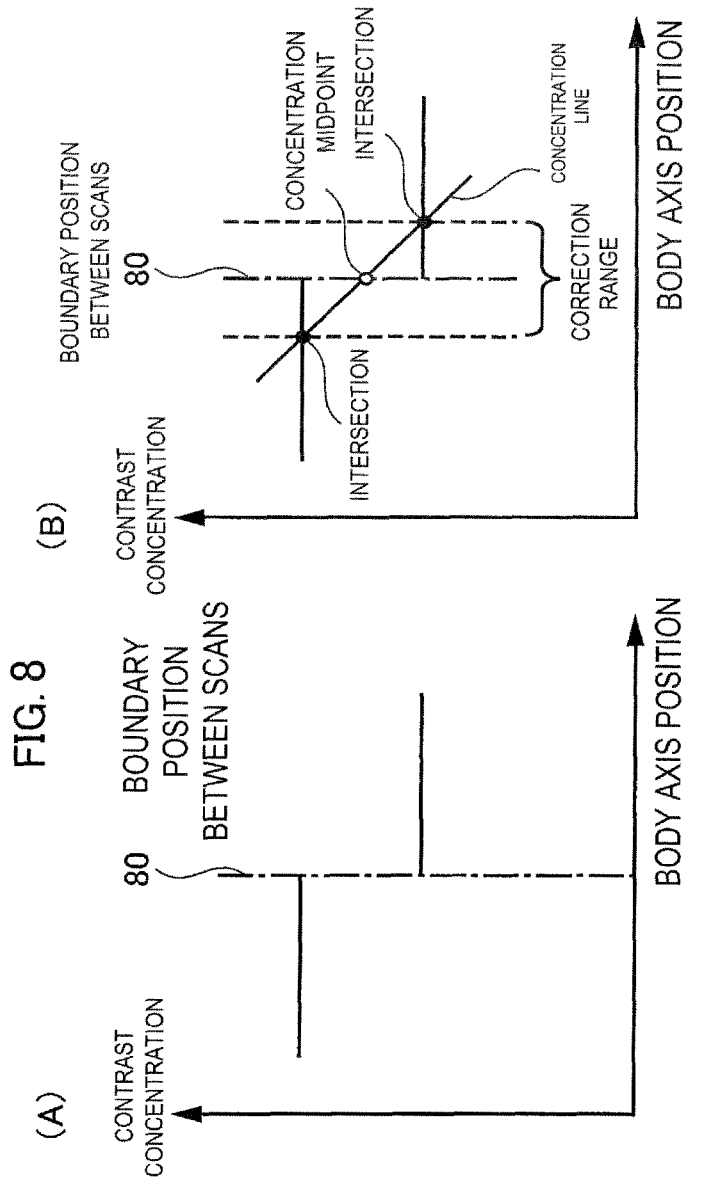
FIG. 8 is an example of the correction range when the time between scans is short.
Figure 9:
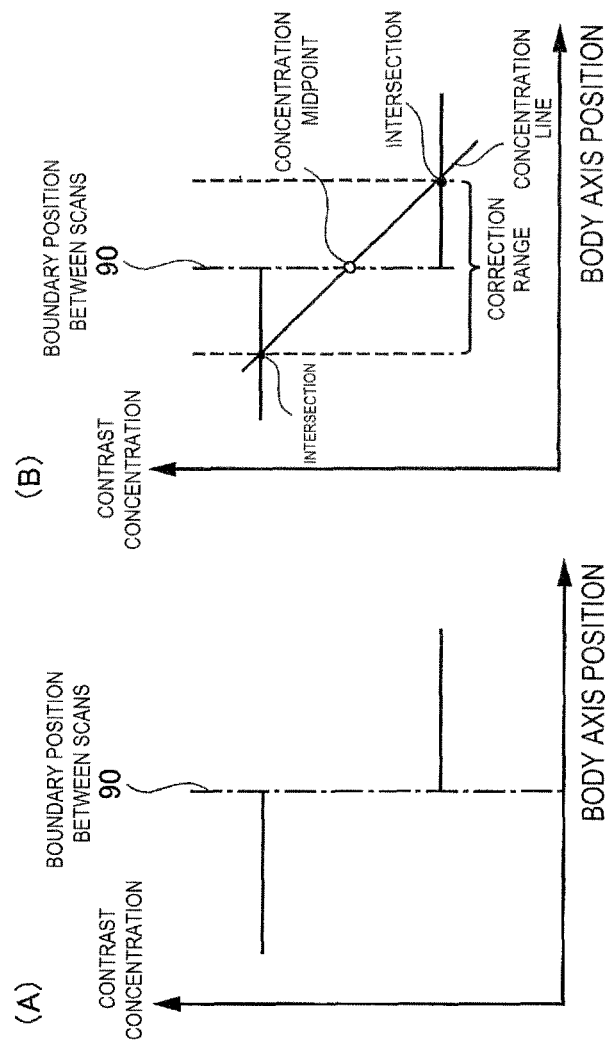
FIG. 9 is an example of the correction range when the time between scans is long.

In addition, the boundary positions between scans 80 and 90 shown in FIGS. 8 and 9 correspond to one of the boundary slices 71, 72, 73, and 74 shown in FIG. 6.

Details of the procedure of calculating the correction range will be described with reference to FIG. 10.

First, as shown in FIG. 10(A), the image processing device 4 acquires a concentration curve C1, which shows a difference in the contrast concentration at a position in the body axis direction, from the pixel values of the pixels corresponding to the original tomographic image group obtained in step S1. In addition, although the concentration curve is shown stepwise in FIG. 10(A) for easy understanding, the concentration curve does not necessarily need to be the stepwise shape.

Then, as shown in FIG. 10(B), the image processing device 4 calculates a concentration difference 81 of the boundary position between scans 80, and calculates the median (concentration midpoint 82).

Then, as shown in FIG. 10(C), the image processing device 4 calculates a concentration line 83 with a certain inclination that passes through the concentration midpoint 82.

Here, the image processing device 4 reduces the inclination of the concentration line 83 when the time between scans is long and increases the inclination of the concentration line 83 when the time between scans is short.

Then, the image processing device 4 calculates two intersections 84 and 85 between the concentration line 83 and the concentration curve C1 as shown in FIG. 10(D), and determines "between the two intersections 84 and 85" as a correction range 86 as shown in FIG. 10(E).

As a result, a wide correction range is obtained when the time between scans is long and the contrast concentration difference 81 is large, and a narrow correction range is obtained when the time between scans is short and the contrast concentration difference 81 is small.

Figure 10:
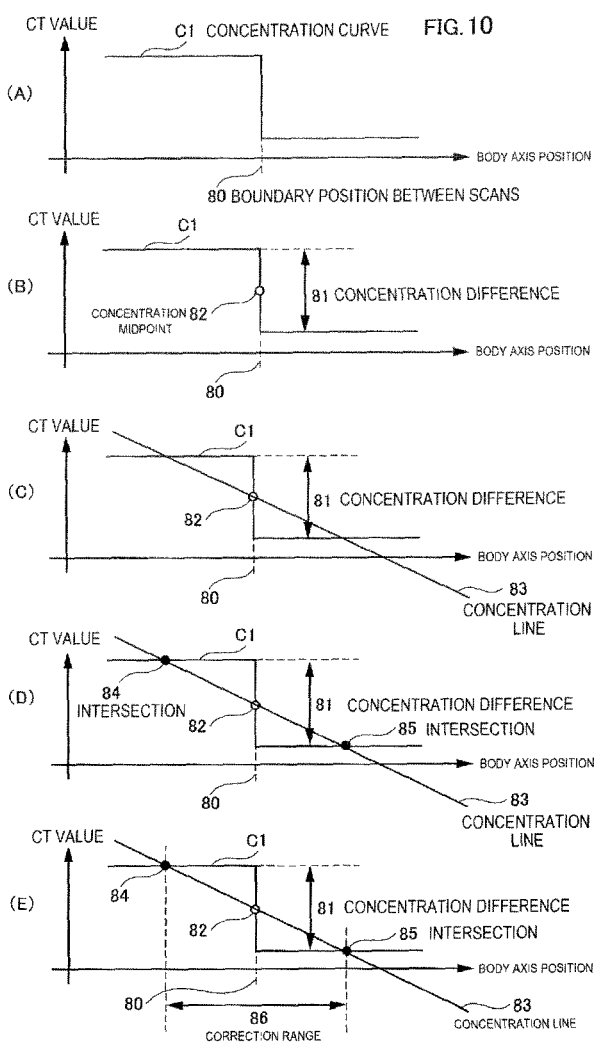
FIG. 10 is a diagram illustrating a method of determining the correction range.
Figure 11:
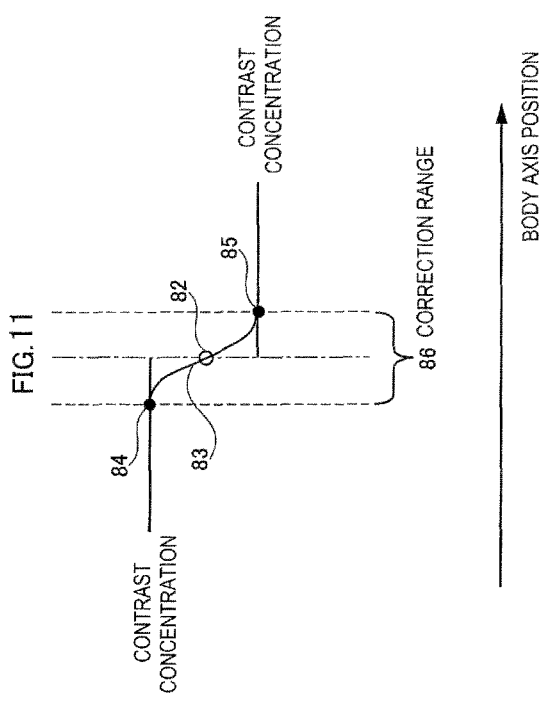
FIG. 11 is another example of the concentration line used for correction.

In addition, the concentration line 83 may be a curve shown in FIG. 11 without being limited to the straight lines shown in FIGS. 8 to 10. In addition, the shape of the concentration line 83 is not limited to these.

In addition, when the X-ray irradiation widths in respective scans are made to overlap each other to acquire projection data during the scan of step S1, projection data of two scans of different data collection time can be acquired at the same body axis position in a section where X-rays overlap.

Therefore, when correcting the tomographic image of the correction range determined in step S3 described above, an image may be generated using the contribution ratio determined according to the length of the time between scans and each projection data of different data collection time, thereby correcting the concentration value unevenness between tomographic images.

In addition, it is preferable to reduce the contribution ratio when the time between scans is short and to increase the contribution ratio when the time between scans is long.

That is, in the overlapping section, projection data of the data collection time t1 and projection data of the data collection time t2 are collected. In the boundary position between scans 80, an image is generated using 50% of the projection data of the data collection time t1 and 50% of the projection data of the data collection time t2. In addition, an image is generated such that the contribution ratio (ratio using the projection data) of projection data distant in time decreases gradually as a distance from the boundary position between scans 80 increases.

Figure 12:
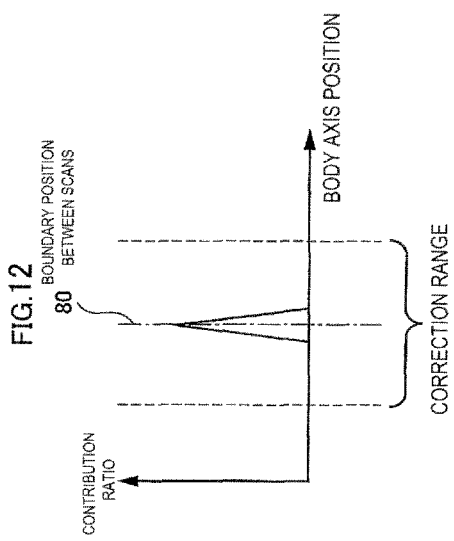
FIG. 12 is a diagram showing the overlap data contribution ratio when the time between scans is short.
Figure 13:
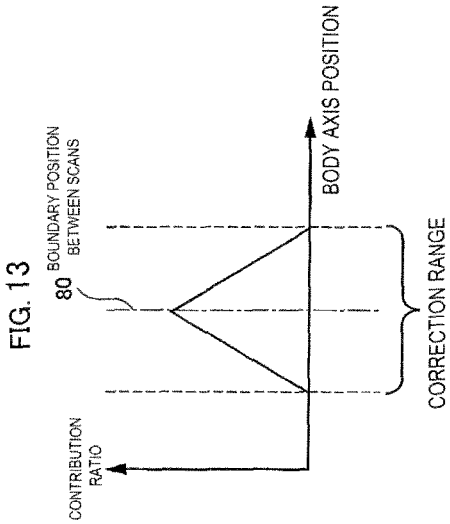
FIG. 13 is a diagram showing the overlap data contribution ratio when the time between scans is long.

In this case, as described above, when the time between scans is short, the change in the concentration of the contrast medium is relatively small. Accordingly, a smooth concentration change is obtained without much correction. When the between scans is shorter than this, the contribution ratio of projection data distant in time is reduced at a position away from the boundary position between scans 80 as shown in FIG. 12. On the other hand, when the time between scans is long, it is not possible to suppress the concentration difference unless correction is performed even at a position away from the boundary slice. Therefore, as shown in FIG. 13, even at a position away from the boundary slice, the contribution ratio of projection data distant in time increased.

After the correction range is determined, the image processing device 4 corrects an image of a boundary portion between scans of the correction range calculated in step S3 (step S4).

In addition, the correction processing may be performed only for a particular contrast portion of each tomographic image.

In this case, it is possible to perform correction processing at high speed for a portion of interest.

Then, the image processing device 4 displays the correction range calculated in step S3 on the image display device 405 together with an image after correction 95 (step S5).

Figure 14:
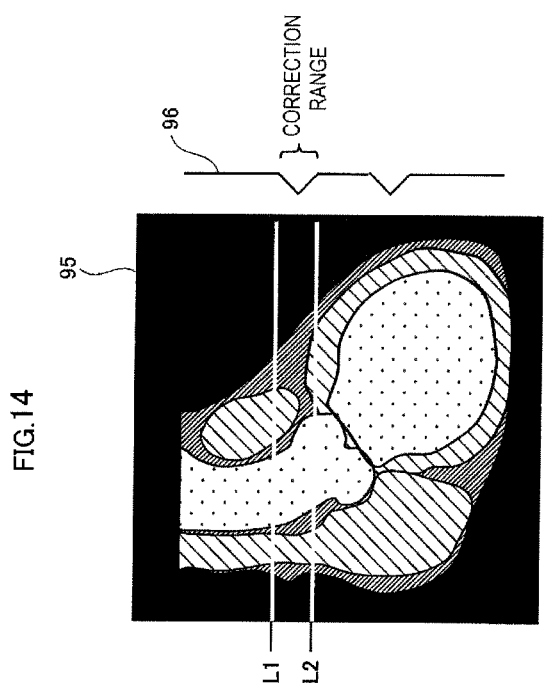
FIG. 14 is a display example showing a correction range or the degree of correction.

For example, as shown in FIG. 14, a start position and an end position of the correction range calculated in step S3 are displayed as lines L1 and L2 on the image after correction 95.

In addition, for example, as shown in FIG. 14, on the image after correction 95 or near the image 95, a graph 96 showing the weighting factor (contribution ratio in the overlapping section) used for correction is displayed so as to correspond to the image position.

Figure 15:
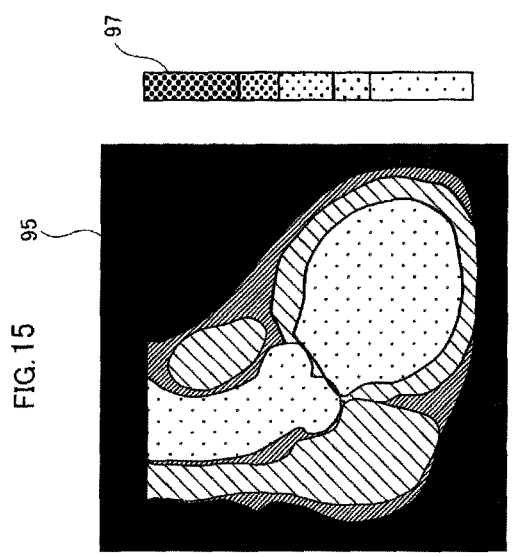
FIG. 15 is another display example showing a correction range and the degree of correction.

Alternatively, as shown in FIG. 15, on the image after correction 95 or near the image 95, a correction bar 97 showing the concentration or color corresponding to the weighting factor (inclination angle of the concentration line or the contribution ratio in the overlapping section) used for correction is displayed an as to correspond to the image position.

In addition, without being limited to these display methods, indices indicating the correction range and the degree of correction, such as a correction range, an inclination angle of the concentration line, and a contribution ratio in the overlapping section, may be displayed using a mark, a graph, a chart, color display, and the like. In addition, only the image after correction 95 may be displayed on the imaged play device 405 without displaying the correction range, or the image after correction 95 and an image before correction may be displayed on the image display device 405 side by side.

As described above, in the X-ray CT apparatus 1 of the invention, projection data in a specific phase of the heart is acquired intermittently in a plurality of time phases at each position of the heart in the body axis direction by emitting X-rays after a predetermined time from the detection of the R wave of the electrocardiogram information to perform a scan, and a tomographic image at each position in the body axis direction is reconstructed on the basis of the acquired projection data (Prospective Triggering Scan). Then, a time between scans from a certain scan to the next scan is calculated on the basis of the electrocardiogram information, and a concentration difference occurring between respective tomographic images is corrected for homographic images of the body-axis-direction range determined according to the length of the calculated time between scans. In addition, an image generated on the basis of the corrected homographic images is displayed, and the corrected body-axis-direction range is displayed.

Therefore, in contrast imaging using the Prospective Triggering method, it is possible to correct concentration unevenness due to discontinuities in time between slices. As a result, it is possible to easily perform image processing, such as processing for extracting an MPR image or a target part without discomfort.

In addition, it is possible to make the concentration change uniform by narrowing the correction range when the time between scans is short and widening the correction range when the time between scans is long.

In addition, in the case of performing a scan by setting an overlapping section between the X-ray irradiation region of a scan at a certain data collection time and the X-ray irradiation region of a scan at the next data collection time, an image may be generated with a contribution ratio, which is determined according to the length of the time between scans, using each projection data of different data collection time.

In this case, if the contribution ratio of the projection data distant in time is reduced when the time between scans is short and the contribution ratio of the projection data distant in time is increased when the time between scans is long, it is possible to obtain an image without concentration unevenness while generating a reliable image using the projection data in each scan.

In addition, if only a contrast portion is set as a target to be corrected, possible to perform correction processing at high speed for a particular part of interest.

In addition, the invention is not limited to the embodiment described above. It is apparent to those skilled in the art that various changes or modifications can be made within the range of the technical idea disclosed in this specification, and it should be understood undoubtedly that they also belong to the technical range of the invention.

REFERENCE SIGNS LIST

1: X-ray CT apparatus
100: gantry
101: X-ray source
105: X-ray detector
109: table
201: X-ray controller
202: gantry controller
203: table controller
204: DAS
3: reconstruction computation unit
4: image processing device
5: electrocardiograph
6: object
C1: concentration curve
80, 90: boundary position between scans
81: concentration difference
82: concentration midpoint
83: concentration line
84, 85: intersection
95: image after correction
96, 97: index of correction

The invention claimed is:

1. An X-ray CT apparatus that acquires a tomographic image of an object by collecting electrocardiogram information of the object from an electrocardiograph, performing a scan in synchronization with the collected electrocardiogram information, and reconstructing projection data obtained by the scan, the X-ray CT apparatus comprising:
An imaging processor configured to implement:
   a data collection unit that acquires projection data in a specific phase of a heart intermittently in a plurality of time phases in each position of the heart in a body axis direction by emitting X-rays at a predetermined timing to perform a scan;
   a reconstruction unit that reconstructs a tomographic image at each position in the body axis direction on the basis of the projection data acquired by the data collection unit;
   a correction unit that calculates a time between scans from a certain scan to a next scan and corrects a contrast concentration difference, which occurs between respective tomographic images, for a tomographic image of a body-axis-direction range determined according to a length of the calculated time between scans; and
   a display unit that displays an image generated on the basis of the tomographic image corrected by the correction unit.

2. The X-ray CT apparatus according to claim 1, wherein the display unit displays the body-axis-direction range corrected by the correction unit together with the generated image.

3. The X-ray CT apparatus according to claim 1, wherein the correction unit narrows a body-axis-direction range of a tomographic image to be corrected when the time between scans is short and widens the body-axis-direction range of the tomographic image to be corrected when the time between scans is long.

4. The X-ray CT apparatus according to claim 1, wherein when the data collection unit performs a scan by setting an overlapping section between an X-ray irradiation region of a scan at a certain data collection time and an X-ray irradiation region of a scan at a next data collection time, the correction unit corrects the contrast concentration difference occurring between respective tomographic images by generating an image using a contribution ratio, which is determined according to the length of the time between scans, and each projection data of different data collection time.

5. The X-ray CT apparatus according to claim 4, wherein the correction unit reduces the contribution ratio when the time between scans is short and increases the contribution ratio when the time between scans is long.

6. The X-ray CT apparatus according to claim 1, wherein the correction unit sets only a contrast portion of the tomographic image as a target to be corrected.

7. An image correction method in an X-ray CT apparatus that acquires a tomographic image of an object by collecting electrocardiogram information of the object from an electrocardiograph, performing a scan in synchronization with the collected electrocardiogram information, and reconstructing projection data obtained by the scan, the image correction method comprising:
   a data collection step of acquiring projection data in a specific phase of a heart intermittently in a plurality of time phases in each position of the heart in a body axis direction by emitting X-rays at a predetermined timing to perform a scan;

a reconstruction step of reconstructing a tomographic image at each position in the body axis direction on the basis of the acquired projection data;

a correction step of calculating a time between scans from a certain scan to a next scan and correcting a contrast concentration difference, which occurs between respective tomographic images, for a tomographic image of a body-axis-direction range determined according to a length of the calculated time between scans; and a display step of displaying an image generated on the basis of the corrected tomographic image.

8. The image correction method according to claim 7, wherein, in the display step, the body-axis-direction range corrected in the correction step is displayed together with the generated image.

9. The image correction method according to claim 7, wherein, in the correction step, a body-axis-direction range of a tomographic image to be corrected is narrowed when the time between scans is short and is widened when the time between scans is long.

10. The image correction method according to claim 7, wherein, when a scan is performed by setting an overlapping section between an X-ray irradiation region of a scan at a certain data collection time and an X-ray irradiation region of a scan at a next data collection time in the data collection step, the contrast concentration difference occurring between respective tomographic images is corrected by generating an image using a contribution ratio, which is determined according to the length of the time between scans, and each projection data of different data collection time in the correction step.

11. The image correction method according to claim 10, wherein, in the correction step, the contribution ratio is reduced when the time between scans is short, and the contribution ratio is increased when the time between scans is long.

12. The image correction method according to claim 7, wherein, in the correction step, only a contrast portion of the tomographic image is set as a target to be corrected.

13. An X-ray CT apparatus that acquires a tomographic image of an object by collecting electrocardiogram information of the object from an electrocardiograph, performing a scan in synchronization with the collected electrocardiogram information, and reconstructing projection data obtained by the scan, the X-ray CT apparatus comprising:

An imaging processor configured to implement:

a data collection unit that acquires projection data in a specific phase of a heart intermittently in a plurality of time phases in each position of the heart in a body axis direction by emitting X-rays at a predetermined timing to perform a scan;

a reconstruction unit that reconstructs a tomographic image at each position in the body axis direction on the basis of the projection data acquired by the data collection unit;

a correction unit that calculates a time between scans from a certain scan to a next scan and corrects a pixel value difference, which occurs between respective tomographic images, for a tomographic image of a body-axis-direction range determined according to a length of the calculated time between scans; and a display unit that displays an image generated on the basis of the tomographic image corrected by the correction unit.

14. The X-ray CT apparatus according to claim 13, wherein when the data collection unit performs a scan by setting an overlapping section between an X-ray irradiation region of a scan at a certain data collection time and an X-ray irradiation region of a scan at a next data collection time, the correction unit corrects the pixel value difference occurring between respective tomographic images by generating an image using a contribution ratio, which is determined according to the length of the time between scans, and each projection data of different data collection time.

* * * * *